United States Patent [19]

King

[11] Patent Number: 5,140,168
[45] Date of Patent: Aug. 18, 1992

[54] TURBIDIMETER SIGNAL PROCESSING CIRCUIT USING ALTERNATING LIGHT SOURCES

[75] Inventor: Karl L. King, Brown Deer, Wis.

[73] Assignee: Great Lakes Instruments, Inc., Milwaukee, Wis.

[21] Appl. No.: 621,150

[22] Filed: Dec. 3, 1990

[51] Int. Cl.⁵ ............................................. G01N 15/06
[52] U.S. Cl. ...................................... 250/575; 356/442
[58] Field of Search ................. 250/574, 575; 73/293; 356/339, 341, 343, 442, 440

[56] References Cited

U.S. PATENT DOCUMENTS

| | | | |
|---|---|---|---|
| 3,775,013 | 11/1973 | Simms | 356/208 |
| 4,131,888 | 12/1978 | Galvin | 250/575 |
| 4,366,384 | 12/1982 | Jensen | 250/575 |
| 4,981,362 | 1/1991 | de Jong et al. | 250/575 |
| 4,999,513 | 3/1991 | Ito et al. | 250/575 |

Primary Examiner—David C. Nelms
Assistant Examiner—K. Shami
Attorney, Agent, or Firm—Quarles & Brady

[57] ABSTRACT

A turbidimeter includes a housing having a cavity with an inlet through which a fluid flows. Two emitters are alternately driven by an alternating signal having a given frequency to transmit modulated light beams through the fluid. Two detectors produce signals representing the intensity of scattered and unscattered light within the fluid. Each of these detector signals is processed to measure the level of the signal component at the given frequency. Such processing includes filtering and phase demodulataing the detector signals to produce a signal indicative of the levels of the component signals at the given frequency. The turbidity is calculated from the signal levels measured as each emitter is excited.

19 Claims, 3 Drawing Sheets

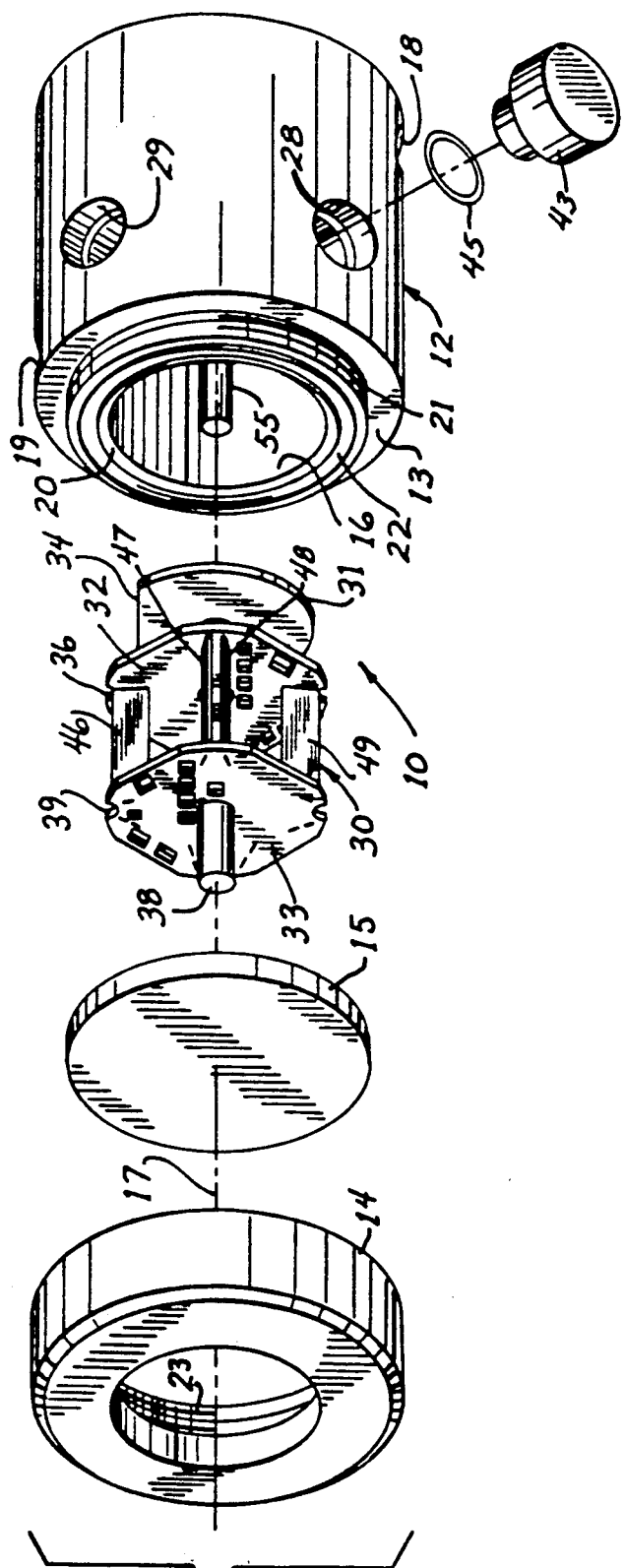

TURBIDIMETER SIGNAL PROCESSING CIRCUIT USING ALTERNATING LIGHT SOURCES

BACKGROUND OF THE INVENTION

The present invention relates to optical apparatus for measuring the turbidity of fluids; and particularly to circuitry for processing signals from light detectors utilized in such apparatus to produce a measurement of the turbidity.

Turbidity is an optical characteristic of a fluid that is related to the presence, nature and amount of suspended matter or particles which scatter light in an otherwise pure fluid. Turbidity may be sensed by instruments commonly known as turbidimeters which measure the characteristic in terms of the amounts of light which are transmitted directly through and scattered by the fluid.

One type of previous turbidimeter utilized a pair of DC light sources to produce light beams of constant intensity and two detectors in which each detector was aligned with a different light source. The light sources were alternately energized and the amounts of light detected by the aligned and unaligned detectors were compared. The DC detector signals produced during energization of each light source were processed to derive a turbidity value, as defined by the U.S. Environmental Protection Agency. Such photoelectric instruments permit turbidity measurements to be conducted on static fluids or those which flow continuously between the emitters and detectors.

The previous turbidimeters used DC amplifiers in the measurement circuitry. Significant errors often existed due to variation of the amplifier's D.C. offset and gain resulting from age and varying operating conditions. As a consequence conventional turbidimeters require frequent recalibration to known turbidity standards. Turbidimeters which used multiple sources and detectors to perform the measurement by comparing the signals from the aligned and unaligned detectors, eliminated much of the gain error. However these devices did not correct for offset errors.

SUMMARY OF THE INVENTION

A turbidimeter in which the present invention can be incorporated comprises a housing within which is defined a cavity through which a fluid can flow to be measured. An inlet is located near one end of the cavity and an outlet is positioned near another end. A first light emitter and a first detector are mounted in an aligned relationship to transmit a first light beam therebetween and through the cavity. A second light emitter and a second light detector also are mounted in an aligned relationship to transmit a second beam of light therebetween and through the cavity. Preferably, the two beams travel along orthogonally related paths.

A generator produces an excitation signal at a given frequency, which can be a multiple or submultiple of the frequency of the alternating supply line voltage which powers the turbidimeter. A switch circuit alternately applies the excitation signal to the first and second emitters. The detector aligned with the excited emitter generates a signal representative of the unscattered light passing through fluid in the cavity. The other detector, which is not aligned with the excited emitter receives light which is scattered due to the fluid turbidity and generates a separate signal representative of the intensity of such scattered light.

The two detector signals are processed by separate, identical signal channels. Each channel includes a means for producing an output signal corresponding to a component signal in the detector signal which component has a frequency equal to the frequency of the excitation signal. The output signals from each channel then are used to derive a turbidity value for the fluid.

A general object of the present invention is to provide an apparatus for measuring the turbidity of a fluid.

A more specific object is to provide a noise immune circuit for determining the turbidity from optical detector signals.

Another object of the present invention is to provide such a circuit which minimizes errors due to variation in signal level offset and gain introduced by amplifiers and other components of the circuit.

A further object is to provide the turbidimeter circuit with automatic gain control to accommodate a fluids having a wide range of turbidity levels.

BRIEF DESCRIPTION OF THE DRAWINGS

FIG. 2 is an exploded view of the turbidimeter;

DETAILED DESCRIPTION OF THE INVENTION

Figure 1:
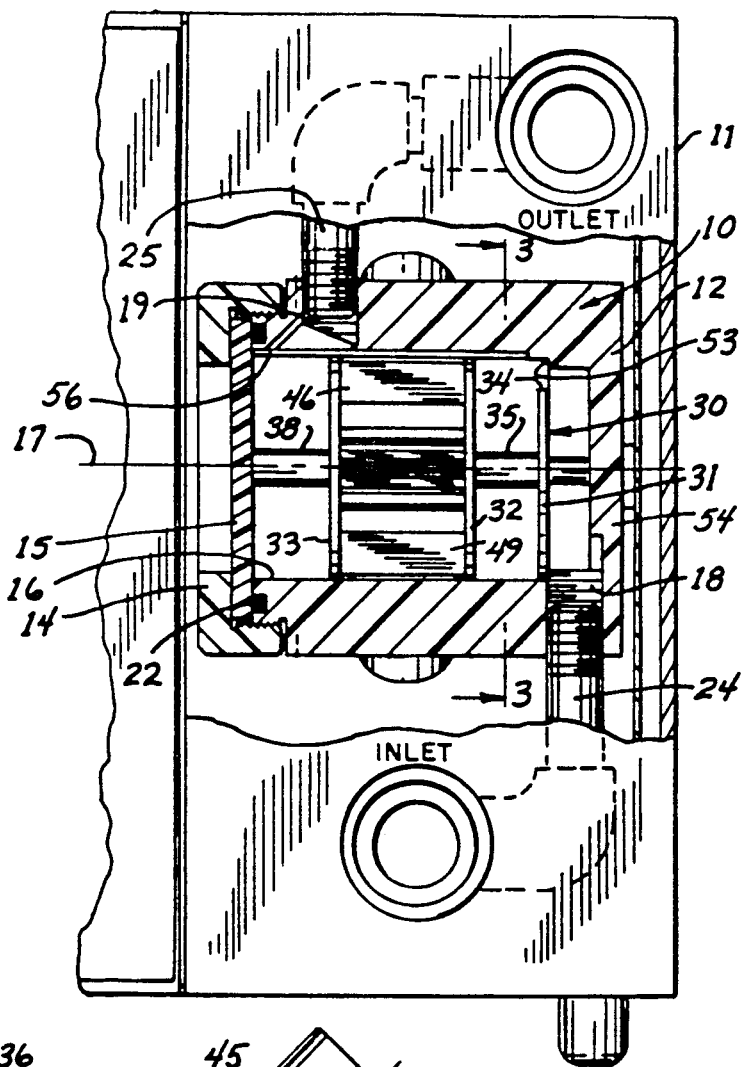
FIG. 1 is a partially cut away diagram of a cabinet which encloses a turbidimeter according to the present invention.

With initial reference to FIGS. 1 and 2, a turbidity sensor 10 is mounted within a cabinet 11. The sensor 10 includes a housing 12 which in the preferred embodiment has a cylindrical shape. The housing 12 consists of a main body 13, annular end cap 14 and a flat, circular end plate 15.

The main body 13 has a cylindrical cavity 16 with a longitudinal axis 17. An inlet opening 18 extends through the main housing near one end of the cavity 16 and an outlet opening 19 extends through the main body near the other end of the cavity. Pipe threads are cut in the housing surfaces forming the inlet and outlet openings 18 and 19 to accept pipe fittings 24 and 25, respectively. As shown in FIG. 1, the turbidity sensor 10 is mounted within the cabinet 11 at an orientation in which the longitudinal axis 17 of the cavity 16 is substantially horizontal. The turbidimeter housing 12 is further positioned so that the inlet opening 18 is at the bottom of the cavity 16 and the outlet opening 19 is at the highest port of the cavity.

The other end of the cavity 16 opens through an annular projection 20 that has external threads 21 on its outer circumferential surface. An O-ring 22 lies within a grove on the planar end surface of projection 20 to provide a fluid tight seal between the main body 13 and the end plate 15. The inner curved surface of the annular end cap 14 has internal threads 23 which engage the external threads 21 on the main body projection 20 when the housing 12 is assembled. This engagement holds the end plate 15 tightly against the main body 13 sealing the cavity 16.

Figure 3:
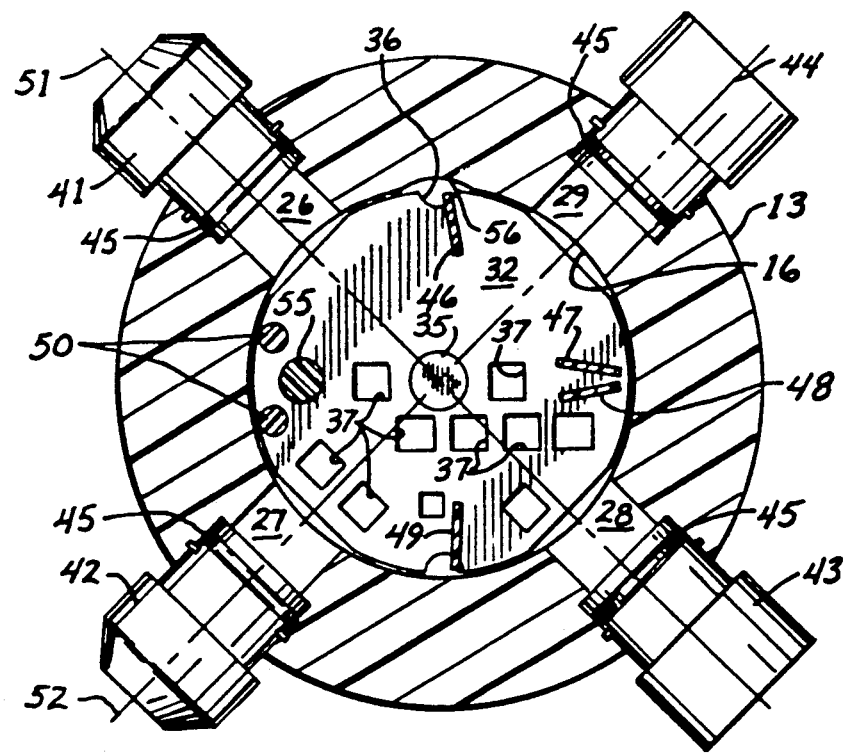
FIG. 3 is a cross sectional view of the turbidimeter along a line indicated in FIG. 1.

Four radial apertures 26, 27, 28 and 29 extend through the cylindrical main body 13 as illustrated in FIG. 3. These apertures preferably lie in a common plane orthogonal to the longitudinal axis 17 of the cavity 16 and between the inlet and outlet openings 18 and 19. The radial apertures 26–29 are spaced at substantially 90 degree increments, for example, around the cavity 16. Specifically, the first radial aperture 26 is centered on a common first radial axis 51 with the third radial aperture 28. Similarly, the second and fourth radial apertures 27 and 29 are centered on a second radial axis 52 which is substantially coplanar with and orthogonal to the first radial axis 51. A first light emitter 41 is located within the first radial aperture 26 and emits a beam of light through the cavity along the first radial axis 51. A second light emitter 42 is mounted within the second radial aperture 27 and emits a beam of light through the cavity along the second radial axis 52. A first light detector 43 is positioned within the third radial aperture 28 and a second light detector 44 is mounted within the fourth radial aperture 29. Fluid tight seals are provided between the main body 13 and each of the light emitters and detectors 41–44 by O-rings 45.

Located within the cavity 16 is a baffle assembly 30 formed by three plates 31, 32 and 33 which lie vertically in the illustrated orientation. The first plate 31 has a generally D-shape with a horizontal straight edge 34 at the upper portion of the plate in the assembled turbidimeter, as illustrated in FIGS. 1, 2 and 3. The curved edge of the first plate 31 has a radius substantially equal to the radius of the cylindrical cavity 16 so that the curved edge of the first plate abuts the inner surface of the cavity. The first plate is fixedly attached near its center to one end of a first spacer 35. When the baffle assembly is placed within the cavity, the edge of the first plate 31 abuts a ridge 53 extending around the inner surface of the cavity near inlet opening 18. This abutment limits the depth to which the assembly 30 can be inserted into the cavity.

With reference to FIGS. 1-3, the other end of the first spacer 35 is attached near the center of the second baffle plate 32. The second plate 32 has a generally square shape with rounded corners conforming to the cylindrical surface of the cavity 16. The upper edge of the second plate 32 contains an indentation 36 providing a gap between the surface of the cavity and the second plate. A number of apertures 37 extend through a lower portion of the second plate. The apertures 37 permit fluid which is introduced into the cavity 16 via inlet opening 18 to flow through the second plate 32, as will be described.

The second and third plates 32 and 33 are spaced from one another by four slat-like vanes 46–49 and two cylindrical posts 50. The ends of the vanes 46–49 are attached to the second and third plates. When the baffle assembly 30 is positioned within the sensor 10, the first vane 46 lies near the curved surface of chamber 16 between the first and third radial apertures 26 and 28 at an acute angle to the second radial axis 52 as shown in FIG. 3. The first vane 46 blocks light produced by the first emitter 41 from traveling in a straight path to the second detector 44. Thus the only way that the second detector 44 can receive light from the first emitter 41 is due to scattering of the light by fluid flowing through the cavity. The second and third vanes 47 and 48 are positioned between the second and third plates 32 and 33 approximately 90 degrees around the edge of the plates from the first vane 46. This positioning of the second and third vanes 47 and 48 places them between the third and forth radial apertures 28 and 29 in the main body. In this location these latter two vanes prevent light from being reflected from the surface of one of the detectors 43 or 44 directly on to the other detector. The fourth vane 49 is located adjacent the cavity surface between the second and third radial apertures 27 and 28 at an acute angle to the first radial axis 51 when the baffle assembly 30 is within cavity 16. The fourth vane 49 blocks light from traveling in a straight line between the second emitter 42 and the first detector 43. Thus, the only way the first detector 43 can receive light from the second emitter 42 is due to scattering of the light by fluid flowing through the cavity. The four vanes 46–49 act as blinders by narrowing the angles of view of the detectors 43 and 44. This limits the amount of stray light reflected by the surfaces of housing 12 and baffle 30 which can reach the detectors.

Referring again to FIGS. 1 and 2, the third plate 33 is spaced from the housing end plate 15 by a second spacer 38. The third plate 33 has a generally square shape with the corners rounded to conform with the curved surface of cavity 16. An indentation 39 is located in the upper most portion of the edge of the third plate. A series of apertures 40 extend through the upper portion of the third plate 33.

A cylindrical retainer post 55 is fixedly attached to end wall 54 of the main body 13 and extends within the cavity 16 parallel to but offset from longitudinal axis 17. Each of the baffle plates 31-33 has a circular aperture through which the retainer post 55 extends when the baffle assembly is inserted into the cavity 16. The engagement of the retainer post 55 with the plates prevents the baffle assembly 30 from rotating within the cavity due to the force of fluid flowing therethrough. The baffle assembly 30 is restricted from moving longitudinally within the cavity 16 by the second spacer 38 abutting end plate 15 and by the first plate 31 abutting a ridge 53 extending around the inner surface of the cavity near inlet opening 18. The components of the baffle assembly 30, the inner surfaces of housing 12 and retainer post 55 all are colored black to reduce their reflectivity.

When the turbidity sensor 10 is coupled to a plumbing system, fluid flows through the inlet opening 18 into the cavity 16 exiting through outlet opening 19. As shown in FIG. 1, the fluid enters the cavity between the first baffle plate 31 and the end wall 54. Because the curved edge of the first plate 31 conforms to the cavity surface, the fluid can flow around the first plate substantially only between the straight edge 34 of the plate and the main body 13 at the upper region of the cavity. Thus the first plate 31 forces the incoming fluid to the upper region of the cavity, i.e. the region above the upper edge 34 of the plate. Since gas bubbles entrained in the fluid are lighter than the fluid, the bubbles flow along a passage created in the upper region between indentation 36 in the second plate 32 and a grove 56 which extends in the main body 13 longitudinally along the upper cavity surface. The passage continues along this grove 56 and through the indentation 39 in the second baffle plate 32 until it reaches the outlet opening 19. The gas bubbles carried by the fluid will flow across the upper region of the cavity and not intersect the radial axes on which the light emitters and detectors 41–44 are located. As a result, the gas bubbles will not interfere with the optical sensing of the fluid turbidity.

However, the cross sectional area of the passage at the upper region of the cavity is relatively small as compared to the size of the inlet and the combined cross sectional areas of the apertures 37 in the second plate 32. As a result, most of the flow volume will be forced downward in a section of the cavity between the first and second plates and through apertures 37. Alternatively, indentations can be provided in edges of the lower half of the second plate 32 to accommodate the fluid flow.

The fluid flows from the apertures 37 in the second baffle plate 32 in a upward angular direction to the apertures 40 in the third plate 33. By vertically offsetting the apertures 37 and 40 in the second and third baffle plates 32 and 33 the fluid is directed through the central region of the cavity formed between the two plates and through the beams of light produced by the emitters 41 and 42. This central region forms the turbidity sensing zone.

Figure 4:
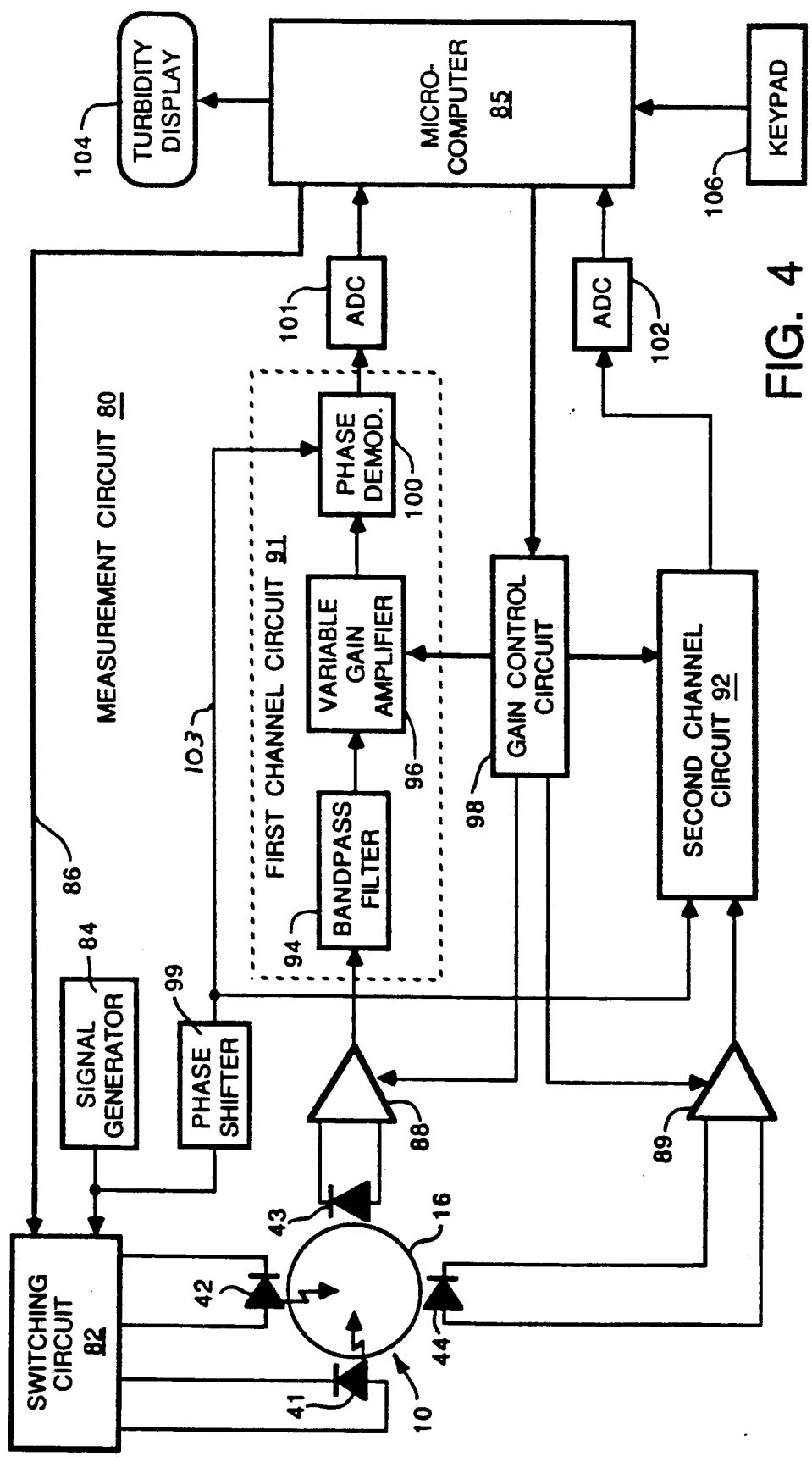
FIG. 4 is a block diagram of the turbidimeter signal processing circuitry.

As shown in FIG. 4, the light emitters 41 and 42 and detectors 43 and 44 are connected to a circuit 80 for deriving a turbidity value based on signals from the detectors. The light emitters 41 and 42 are connected by a switching circuit 82 to a signal generator 84. The signal generator 84 produces a sinusoidal excitation signal at a given frequency which drives the light emitters 41 and 42. Preferably, the excitation signal has a frequency which is an even multiple or submultiple of the frequency (50 or 60 Hertz) of the AC power line voltage that supplies power to turbidimeter circuit 80. Thus the excitation signal frequency f can be expressed by the function:

$$f = (2n)^{\pm 1} f_{pl} \quad (1)$$

wherein n is a non-zero, positive integer and $f_{pl}$ is the AC power line frequency. A submultiple is preferred, for example 15 Hertz for a 60 Hertz supply frequency, so that harmonics of the AC line frequency will not appear as signal contaminants. The switching circuit 82 normally alternates applying the sinusoidal excitation signal to one of the emitters at a time in response to a control signal on line 86 from a microcomputer 85. The microcomputer alternatively can place the switching circuit 82 in another mode in which neither light emitter receives the excitation signal from generator 84.

When one of the light emitters 41 or 42 is excited, the light detector 43 or 44 which is aligned with the energized emitter receives light directly from that emitter through the fluid within cavity 16. The other, non-aligned light detector receives light which is scattered due to the turbidity of the fluid.

In a first phase of operation the microcomputer 85 sends a command via line 86 which causes switching circuit 82 to couple the first light emitter 41 to the output of signal generator 84. This command also decouples the second emitter 42 from the signal generator 84. Thus, the first emitter 41 is energized by the fifteen Hertz excitation signal from the generator 84 to produce a light beam that is modulated at that frequency. This light beam travels along axis 51 (FIG. 3) toward the first light detector 43. The turbidity of the fluid within cavity 16 scatters some of the light so that only a fraction of it reaches the first detector 43 which is aligned with the first emitter 41. Some of the scattered light impinges the second detector 44. Therefore, in this phase of the operation, the first detector 43 produces an output signal corresponding to the unscattered light from the first emitter, whereas the second detector 44 produces a signal corresponding to the scattered light due to the turbidity of the fluid within cavity 16. Each detector output signal is an alternating signal having predominant component at fifteen Hertz due to the excitation frequency modulating the first emitter 41. The amplitude of this component signal corresponds to the intensity of the received light.

The signals from the detectors 43 and 44 are amplified by a preamplifier 88 or 89, respectively. The gain of the preamplifiers 88 and 89 is controlled by a gain control circuit 98, as will be described. The output signals from the two preamplifiers 88 and 89 are processed separately in parallel by either a first channel circuit 91 or a second channel circuit 92. The circuitry in the two channels is identical with the detailed circuitry being shown for the first channel circuit 91. In this channel, a bandpass filter 94 receives the output signal from the first preamplifier 88. The bandpass filter 94 has a transmission band that includes the frequency of the excitation signal and excludes harmonics and sub-harmonics of that frequency. This filtering significantly reduces the amplitude of component frequencies within the detector signal that are outside a narrow frequency band centered at the excitation signal frequency.

The filtered signal then is applied to a variable gain amplifier 96 which amplifies the signal by a factor determined by a gain control circuit 98. Specifically, the gain control circuit 98 receives a digital signal from microcomputer 85 indicating the degree to which the incoming signals from the first detector 43 should be amplified. The microcomputer 85 adjusts the gain applied to the detector signals depending upon the degree of turbidity in the fluid being sensed so as to produce values at the microcomputer inputs from which the turbidity can be calculated. In response to this digital value, the gain control circuit 98 produces a signal which adjusts the gain of first preamplifier 88 and amplifier 96 in the first channel circuit 91. The gain control circuit 98 produces a similar set of control signals for the second preamplifier 89 and a variable gain amplifier in the second channel circuit 92.

In this initial phase, the signal from the first detector 43, produced by the unscattered light, has a significantly larger amplitude than the signal from the second detector 44, produced by the scattered light. Thus, in the first phase of the operation, the gain of the first preamplifier 88 and the variable gain amplifier 96 which process the unscattered light signal are set to a lower value than the corresponding gains of the second preamplifier 89 and the amplifier within the second channel circuit 92 which process the weaker signal produced by the scattered light. In both instances, the gains are chosen to produce acceptable digital values at the corresponding inputs of microcomputer 85. Furthermore, the variable gain preamplifiers and amplifiers enable the turbidimeter to have multiple ranges of sensitivity which are automatically chosen by the microcomputer 85 based on the magnitude of the measurements it receives. As will be described, the microcomputer utilizes these gain factors to normalize the input data when mathematically calculating the turbidity.

With continuing reference to the processing in the first channel circuit 91 of FIG. 4, the signal at the output of the variable gain amplifier 96 is applied to a phase demodulator 100. The phase demodulator 100 processes the signal to produce a D.C. output signal indicative of the average level of the A.C. input signal at the excitation signal frequency which drives the light emitters 41 and 42. In order to perform this demodulation, the phase demodulator 100 receives a reference signal via line 103 from phase shifter 99 that is produced by phase shifting the excitation signal from generator 84. This phase shifting accounts for the phase shift of the detector signal produced by the bandpass filter 94 and the preamplifier 88. The phase shifter 99 also includes a zero crossing detector which transforms the phase shifted sinusoidal excitation signal into a square wave reference signal that alternates between high and low digital logic levels. The resultant reference signal is applied to the phase demodulator 100 and to a similar phase demodulator within the second channel circuit 92. In the exemplary system a fifteen Hertz reference signal is produced on line 103 that is in phase with the fifteen Hertz component of the unscattered and scattered light signals from the first and second detectors 43 and 44, respectively.

The phase demodulator 100 uses the square wave reference signal to switch the gain of an internal amplifier between +1 and −1 at the frequency of the signal that excites the emitters 41 and 42. Therefore, the phase demodulator 100 is tuned to the excitation signal frequency. Component signals in the output of the variable gain amplifier that are at frequencies other than the excitation signal frequency are rejected in the phase demodulator 100. Harmonics of the excitation signal frequency are cancelled, regardless of their phase relationship to the reference signal. Thus, the resultant output from the phase demodulator 100 is a D.C. signal having a level corresponding to the amplitude of the detector signal component at the light emitter excitation frequency. Similar processing is conducted by the second channel circuit 92 on the signal produced by the second light detector 44.

The processed detector signals from the first and second channel circuits 91 and 92 are applied to inputs of two analog-to-digital converters (ADC) 101 and 102. Each ADC is a standard dual-slope converter which electrically integrates the input signal for a fixed time period. At the end of that period, a reference voltage of opposite polarity is applied to the input of the integrator and a timer mechanism is initialized. When the value of the integrator returns to zero, the integration process is stopped and the time interval that elapsed during the deintegration process is read. This deintegration time interval is proportional to the average value of the output signal from the associated channel circuit 91 or 92. The integral of a sinusoid over an integral number of periods is zero. Thus, any signal level offset errors due to line voltage signals or their harmonics are eliminated by setting the fixed integration period of the converters 101 and 102 to an integral multiple of the power line voltage period.

In a typical installation of the turbidimeter, alternating electric fields from numerous sources, such as power lines and RF interference, may affect the signals produced by the light detectors 43 and 44. By bandpass filtering, phase demodulating and digitizing the detector signal in this manner, extraneous component signals are rejected from the detector signal in the first channel circuit 91, thereby producing a signal at the output of the circuit which accurately represents the intensity of the light sensed by the first detector 43.

The digital output of the first analog-to-digital converter 101 is coupled to one input port of the microcomputer 85 and the digital output of the second analog-to-digital converter 102 is coupled to another input port. The microcomputer 85 includes a microprocessor, memory for storing data and a program for the microprocessor, and input/output circuits. A keypad 106 is coupled to the microcomputer to enable the user to input setup parameters and control the turbidimeter operation. A display 104 includes a means for numerically displaying the measured turbidity and indicators of the turbidimeter status.

After a period of time from when the command was sent to switching circuit 82, the microcomputer 85 reads and stores the values applied to the two input ports by the analog-to-digital converters 101 and 102. These values, designated $V_1$ and $V_2$, represent the intensity of the light from the first emitter 41 received by each of the detectors 43 and 44, which in the first phase of operation represent the intensities of the unscattered and scattered light, respectively.

Once the first set of light intensity values ($V_1$ and $V_2$) has been stored, the microcomputer 85 transmits another command via control line 86 instructing the switching circuit 82 to enter the second phase of operation. This second command causes the switching circuit to disconnect the first emitter 41 from the signal generator 84 and couple the second emitter 42 to the signal generator. This switching process applies the excitation signal from the signal generator 84 to the second emitter 41 causing it to produce a light beam which is modulated at that signal's frequency. In this second phase of operation, the second detector 44 is aligned with the excited emitter 42 and produces a signal from the unscattered light passing through the fluid in cavity 16. Similarly the first detector 43 now receives light scattered by the turbidity of the fluid.

At this time, the microcomputer 85 also transmits new commands to the gain control circuit 98 to alter the preamplifiers 88 and 89 and the variable gain amplifiers 96 in the first and second channel circuits 91 and 92. In the second mode of operation, the first channel circuit 91 will process the relatively weak signal due to the scattered light and the second channel circuit 92 will process the stronger unscattered light signal. Thus the gains applied to the detector signals must be reversed in the second phase.

The processing of the signals in the second phase of operation is identical to that previously described with respect to the first phase; with the obvious exception that the microcomputer 85 now receives a value ($V1'$) from the first analog-to-digital converter 101 which corresponds to the intensity of the scattered light, while the value ($V2'$) received from the second analog-to-digital converter 101 corresponds to the unscattered light intensity. The values from analog-to-digital converter 101 and 102 are read, processed and stored by the microcomputer 85 in the same manner as the signals in the first phase of operation.

The output values from the analog-to-digital converters 101 and 102 represent direct currents and can include D.C. level offset errors, such as were present in previous D.C. type turbidimeters. These offset errors can be measured and removed by periodically operating the measurement circuit 80 without applying light to the detectors 43 and 44. During this offset error measurement mode, the microcomputer 85 disables the switching circuit 82 from exciting either of the light emitters 41 or 43. Since the turbidimeter has a sealed cavity 16, light will not reach either of the detectors 43 or 44 during this mode of operation. Thus, the output of the two analog-to-digital converters 101 and 102 during this "dark" mode corresponds solely to the D.C. offset errors. The dark mode output values are read by the microcomputer 85 and stored for subsequent use in compensating the turbidity measurement calculation for the offset errors.

Once light intensity values have been stored for both phases of operation, the microcomputer 85 calculates the turbidity of the fluid by first solving the equation:

$$K = \sqrt{\left(\frac{V2}{V1}\right)\left(\frac{V1'}{V2'}\right)} \quad (2)$$

where V1 is the output of the first detector 43 representing the unscattered light intensity during the first phase of operation, V2 is the output of the second detector 44 representing the scattered light intensity during the first phase of operation, V1' is the output of the first detector 43 representing the scattered light intensity during the second phase of operation, and V2' is the output of the second detector 44 representing the unscattered light intensity during the second phase of operation.

Although at relatively low turbidities the value of K is proportional to the turbidity, in general K is a non-linear function of turbidity. Therefore, the value of K addresses a look-up table stored in the memory of microcomputer 85, from which the actual turbidity value is read. The look-up table contains a finite number of turbidity values ($\phi 1, \phi 2, \ldots, \phi n$) which are associated with a finite number of the values of K (K1, K2, ..., Kn, respectively). If the calculated value for K equals one of those for which a turbidity value has been stored in the look-up table, the turbidity value merely is read from the table. However more often the calculated value of K will be between two values ($K_i$ and $K_{i+1}$) for which turbidity values ($\phi_i$ and $\phi_{i+1}$) have been stored in the look-up table. In this case, the turbidity value $\phi$ for the value of K is found by standard linear interpolation using the look-up table values and the expression:

$$\phi = \frac{(K - K_i)(\phi_{i+1} - \phi_i)}{(K_{i+1} - K_i)} \quad (3)$$

Other techniques than a look-up table and interpolation can be used to derive the turbidity value.

As noted previously, the analog-to-digital converters 101 and 102 are direct current circuits and can add a D.C. level offset error to the detector signal being processed. This offset error can be measured for each channel 91 and 92 and stored within the microcomputer 85 during the dark mode. The error values arithmetically adjust the light intensity values V1, V2, V1' and V2' to remove the offset error prior to calculating turbidity. In addition, the four light intensity values are normalized to account for the different gain factors applied by the corresponding preamplifiers and variable gain amplifiers.

I claim:

1. An apparatus for measuring turbidity of a material comprising:
   an emitter which when excited transmits a light beam through the material;
   means for exciting said emitter with an alternating signal having a given frequency;
   a first detector for producing a first detector signal representative of an intensity of light travelling in substantially in a straight line through the material from said emitter;
   a second detector for producing a second detector signal representative of an intensity of light from said emitter which is scattered within the material;
   a means for producing a first output signal corresponding to a magnitude of a component of the first detector signal at the given frequency;
   a means for producing a second output signal corresponding to a magnitude of a component of the second detector signal at the given frequency; and
   means for determining the turbidity of the fluid in response to the first and second output signals.

2. The apparatus as recited in claim 1 wherein the given frequency is selected from a group of frequencies which are multiples and sub-multiples of the frequency of an alternating supply voltage which powers the turbidimeter.

3. The apparatus as recited in claim 1 wherein both said means for producing a first output signal and said means for producing a second output signal includes an electronic filter having a transmission band which includes the given frequency and which does not include harmonics of the given frequency.

4. The apparatus as recited in claim 1 wherein said means for producing a first output signal and said means for producing a second output signal each include a phase demodulator tuned to the given frequency.

5. The apparatus as recited in claim 1 wherein said means for producing a first output signal and said means for producing a second output signal each comprise:
   a filter which receives the corresponding detector signal and which has a transmission band that includes the given frequency;
   a variable gain amplifier having an input coupled to said filter; and
   a phase demodulator for detecting a component signal at the given frequency contained in a signal from said amplifier.

6. The apparatus as recited in claim 1 wherein said means for producing a first output signal and said means for producing a second output signal each include a dual-slope analog-to-digital converter with a integration time that is substantially equal to an integral multiple of a period of an alternating supply voltage which powers the turbidimeter.

7. The apparatus as recited in claim 1 further comprising:
   means for deriving a first error signal from the first output signal when light is not impinging said first detector;
   means for deriving a second error signal from the second output signal when light is not impinging said second detector;
   means for combining the first error signal with the first output signal when light is impinging said first detector to produce a first compensated output signal; and
   means for combining the second error signal with the second output signal when light is impinging said second detector to produce a second compensated output signal.

8. An apparatus for measuring turbidity of a material comprising:
   a first emitter which when excited transmits a first light beam into the material;
   a second emitter which when excited transmits a second light beam into the material, the second light beam being transverse to the first light beam;

means for exciting said first and second emitters one at a time with an alternating signal having a given frequency;

a first detector positioned to receive light traveling in a straight line through the material from said first emitter and producing a first detector signal indicating the intensity of light received by said first detector;

a second detector positioned to receive light traveling in a straight line through the material from said second emitter and producing a second detector signal indicating the intensity of light received by said second detector;

a means for producing a first output signal corresponding to a magnitude of a signal component of the first detector signal at the given frequency;

a means for producing a second output signal corresponding to a magnitude of a component of the second detector signal at the given frequency;

means for sampling the first and second output signals while the first emitter is being excited to produce a first pair of light intensity values and while the second emitter is being excited to produce a second pair of light intensity values; and processor means for deriving the turbidity of the fluid from the first and second pairs of light intensity values.

9. The apparatus as recited in claim 8 wherein the given frequency is selected from a group of frequencies which are multiples and sub-multiples of the frequency of an alternating supply voltage which powers the turbidimeter.

10. The apparatus as recited in claim 8 wherein said means for producing a first output signal and said means for producing a second output signal each include a filter having a transmission band which includes the given frequency and which does not include harmonics of the given frequency.

11. The apparatus as recited in claim 8 wherein said means for producing a first output signal and said means for producing a second output signal each include a phase demodulator tuned to the given frequency.

12. The apparatus as recited in claim 8 wherein said means for producing a first output signal and said means for producing a second output signal each comprise:

a filter which receives the corresponding detector signal and which has a transmission band that includes the given frequency;

a variable gain amplifier having an input coupled to said filter; and a phase demodulator for detecting a component signal at the given frequency contained in a signal from said amplifier.

13. The apparatus as recited in claim 8 wherein said means for producing a first output signal and said means for producing a second output signal each include a dual-slope analog to digital converter having a signal integration time that is substantially equal to an integral multiple of a period of an alternating voltage which powers the turbidimeter.

14. The apparatus as recited in claim 8 wherein said processor derives a value K according to the following equation:

$$K = \sqrt{\left(\frac{V2}{V1}\right)\left(\frac{V1'}{V2'}\right)}$$

where V1 is a level of the first output signal when said first emitter is excited, V2 is a level of the second output signal when said first emitter is excited, V1' is a level of the first output signal when said second emitter is excited, and V2' is a level of the second output signal when said second emitter is excited; and the processor derives a turbidity value from the value of K.

15. The apparatus as recited in claim 8 wherein said processor means further comprises:

means for deriving a first error signal from the first output signal when light is not impinging said first detector;

means for deriving a second error signal from the second output signal when light is not impinging said second detector;

means for combining the first error signal with the first output signal when light is impinging said first detector to produce a first compensated output signal; and means for combining the second error signal with the second output signal when light is impinging said second detector to produce a second compensated output signal; and wherein the turbidity is derived by said processor means from the compensated output signals.

16. An apparatus for measuring turbidity of a fluid comprising:

a body having a cavity through which the fluid can flow;

a first emitter for transmitting a first light beam through the cavity when said first emitter is excited;

a second emitter for transmitting a second light beam through the cavity when said second emitter is excited, the second light beam being substantially coplanar with and substantially orthogonal to the first light beam;

means for exciting said first and second emitters one at a time with an alternating signal having a given frequency;

a first detector positioned to receive light traveling in a straight line through the cavity from said first emitter and producing a first detector signal representative of received light intensity;

a second detector positioned to receive light traveling in a straight line through the cavity from said second emitter and producing a second detector signal representative of received light intensity;

a first signal channel comprising a first bandpass filter receiving the first detector signal and having a transmission band that includes the given frequency, a first variable gain amplifier having an input coupled to said first bandpass filter, and a first phase demodulator for detecting a component signal at the given frequency contained in a signal from said first variable gain amplifier and producing a first output signal indicative of the magnitude for that component signal; and a second signal channel comprising a second bandpass filter receiving the second detector signal and having a transmission band that includes the given frequency, a second variable gain amplifier having an input coupled to said second bandpass filter, and a second phase demodulator for detecting a component signal at the given frequency contained in a signal from said second variable gain amplifier and producing a second output signal indicative of the magnitude for that component signal; and processor means for deriving the turbidity of the fluid from the first and second output signals and controlling the gain of said first and second variable gain amplifiers.

17. The apparatus as recited in claim 16 wherein both said first and second signal channel further comprise a dual-slope analog to digital converter receiving the output signal produced by the phase demodulator for that channel, and having a signal integration time substantially equal to an integral multiple of a period of an alternating voltage that powers the turbidimeter.

18. The apparatus as recited in claim 16 wherein said processor derives a value K according to the following equation:

where V1 is a level of the first output signal when said first emitter is excited, V2 is a level of the second output signal when said first emitter is excited, V1' is a level of the first output signal when said second emitter is excited, and V2' is a level of the second output signal when said second emitter is excited; and the processor derives a turbidity value from the value of K.

19. The apparatus as recited in claim 16 wherein said processor means further comprises:

means for deriving a first error signal from the first output signal when light is not impinging said first detector;

means for deriving a second error signal from the second output signal when light is not impinging said second detector;

means for combining the first error signal with the first output signal when light is impinging said first detector to produce a first compensated output signal; and means for combining the second error signal with the second output signal when light is impinging said second detector to produce a second compensated output signal.

* * * * *

UNITED STATES PATENT AND TRADEMARK OFFICE
CERTIFICATE OF CORRECTION

PATENT NO. : 5,140,168
DATED : August 18, 1992
INVENTOR(S) : Karl L. King It is certified that error appears in the above-identified patent and that said Letters Patent is hereby corrected as shown below:

In Column 13 after Line 20, insert:

$$K = \sqrt{\left(\frac{V2}{V1}\right)\left(\frac{V1'}{V2'}\right)}$$

Signed and Sealed this

Nineteenth Day of October, 1993

Attest:

BRUCE LEHMAN

*Attesting Officer*   *Commissioner of Patents and Trademarks*